United States Patent [19]

Waddan

[11] 4,088,672

[45] May 9, 1978

[54] PREPARATION OF DICYANOBUTENES FROM 3-PENTENENITRILE

[75] Inventor: Dhafir Yusuf Waddan, Manchester, England

[73] Assignee: Imperial Chemical Industries Limited, London, England

[21] Appl. No.: 571,560

[22] Filed: Apr. 25, 1975

Related U.S. Application Data

[63] Continuation of Ser. No. 387,724, abandoned.

[30] Foreign Application Priority Data

Aug. 18, 1972 United Kingdom ............... 38624/72

[51] Int. Cl.$^2$ .................. C07C 120/00; C07C 121/20
[52] U.S. Cl. ............................................. 260/465.8 R
[58] Field of Search ................. 260/465.8 D, 465.8 R

[56] References Cited

U.S. PATENT DOCUMENTS

| 3,261,879 | 7/1966 | Banks | 260/683 |
| 3,365,513 | 1/1968 | Heckelsberg | 260/683 |
| 3,974,196 | 8/1976 | Nakamura et al. | 260/465.8 R |

FOREIGN PATENT DOCUMENTS

| 1,285,431 | 8/1972 | United Kingdom | 260/465.8 R |

*Primary Examiner*—Joseph Paul Brust
*Attorney, Agent, or Firm*—Cushman, Darby & Cushman

[57] ABSTRACT

Dinitriles are obtained by heating an olefinically unsaturated mononitrile in presence of an olefin disproportionation catalyst, for example, 3-pentenenitrile gives dicyanobutenes.

8 Claims, No Drawings

PREPARATION OF DICYANOBUTENES FROM 3-PENTENENITRILE

This is a continuation of application Ser. No. 387,724 filed Aug. 13, 1973, now abandoned.

This invention relates to the manufacture of dinitriles and more especially to the manufacture of dinitriles from mononitriles.

Dinitriles are of particular value in synthetic organic chemistry because they may be converted on the one hand to diamines by hydrogenation and, on the other, to dicarboxylic acids by hydrolysis. Diamines and dicarboxylic acids are valuable because the presence of two functional centres in the molecule enables large molecules to be built up from smaller. Particularly important are the condensation polymers prepared by condensing two different bifunctional compounds, for example polyesters made by condensing a glycol with a di-acid, and polyamides made by condensing a diamine with a di-acid.

Dinitriles may be made by a number of synthetic methods. In certain cases dinitriles may be made by the dimerisation of olefinically unsaturated mononitriles, for example acrylonitrile may be converted to adiponitrile by electrolytic methods or by reaction with an alkali metal amalgam in a medium containing a proton source. Catalytic methods for the same conversion are also available but the yields are generally indifferent.

According to our invention dinitriles may be obtained from olefinically unsaturated mononitriles which are generally different from those used as starting materials in the dimerisation processes already mentioned.

Our invention provides a process for the manufacture of dinitriles which comprises heating an olefinically unsaturated mononitrile in the presence of an olefin disproportionation catalyst.

By an olefin disproportionation catalyst we mean a catalyst useful in the disproportionation of olefins. Such catalysts are described, for example, in Catalysis Reviews, 3, 37 (1969) and in Russian Chemical Reviews 40 (8), 669 (1971). They are transition metal catalysts and particularly important are compounds of tungsten, molybdenum and rhenium. Suitable compounds are the oxides and the carbonyls and such compounds are conveniently supported on catalyst supports, for example alumina or silica. Alternatively the catalyst compounds may be used in unsupported form and in this connection tungsten hexachloride is particularly suitable, especially when used in conjunction with a reducing agent, especially a metal alkyl such as ethyl-aluminum dichloride or butyl lithium, or a metal hydride. In certain instances the activity of molybdenum or tungsten catalysts may be promoted by the presence of another metal, especially cobalt or chromium. Other transition metals, the compounds of which may be used as catalysts in the process of our invention, include rhodium, iridium, osmium, ruthenium, niobium, tantalum, tellurium, lanthanum, thorium, vanadium, and tin. Such compounds may be used in admixture with each other or with compounds of molybdenum, tungsten or rhenium.

In the process of our invention an olefinically unsaturated mononitrile is converted to a dinitrile. Effectively this results from the linking of that part of the molecule of the mononitrile which contains the nitrile group and which is separated from the other part of the molecule by the olefinic double bond with the corresponding part of an identical molecule of mononitrile. Thus a mononitrile $R = R'.CN$, where R and R' are hydrocarbon residues will give a dinitrile $CN.R' = R'.CN$, although the olefinic double is subject to rearrangement and will not necessarily be in the position shown. Uncyjugated mononitriles, that is those in which the olefinic double bond is separated from the nitrile group by at least one saturated carbon atom are preferred to conjugated nitriles.

Thus, 3-pentenenitrile is converted to a mixture of 1,4-dicyanobutenes. 1,4-dicyanobutenes may be hydrogenated by known methods to adiponitrile which in turn may be hydrogenated to hexamethylenediamine, or under certain conditions, the conversion to hexamethylenediamine may be effected in one step. Hexamethylenediamine is suitable for polycondensation with dicarboxylic acids, to give polyamides, for example with adipic acid to give polyhexamethylene adipamide (nylon 6,6), a polyamide suitable for moulding or for melt spinning into synthetic fibres.

The process of our invention is effected by heating the mononitrile in the presence of the catalyst. Heating may take place over a wide range of temperature, for example from 20° to 450° C with preferred temperatures in the range 80° to 200° C. The process may be conducted in either the liquid or the vapour phase. Pressures are not critical and the process may be conducted at atmospheric pressure or even below, or at moderately raised pressures, say up to 50 atmospheres. The contact time with the catalyst may vary widely, for example from a fraction of a second (e.g. 0.1 second) up to several hours (e.g. 10 hours).

After the reaction has progressed to the desired degree, the dinitrile is separated from unchanged mononitrile catalyst and by-products by any suitable means. Fractional distillation, if necessary under reduced pressure, is a very suitable method in many cases.

The invention is illustrated but not limited by the following Example in which the parts and percentages are by weight.

EXAMPLE

A mixture of 3-pentenenitrile (3.2 parts), molybdenum hexacarbonyl (0.25 parts) and tungsten hexachloride (0.25 parts) was boiled under reflux for 4 hours. Gas-liquid chromatographic analysis of the product showed that it contained cis-1,4-dicyanobutene-1: 20%
trans-1,4-dicyanobutene-1: 3%
1,4-dicyanobutene-2: 5%
3-pentene nitrile: 60%.

This corresponds with a 40% conversion of 3-pentenenitrile, 70% of the product being 1,4-dicyanobutenes useful for conversion to hexamethylenediamine.

The dicyanobutenes were separated by fractional distillation.

I claim:

1. A process for the manufacture of dicyanobutenes from 3-pentenenitrile consisting essentially of heating an olefinically unsaturated feed consisting essentially of 3-pentenenitrile at 20° to 450° C with an olefin disproportionation catalyst selected from the group consisting of an oxide or carbonyl of tungsten, molybdenum, rhenium, rhodium, iridium, osmium, ruthenium, niobium, tantalum, tellurium, lanthanum, thorium, vanadium, or tin, tungsten hexachloride or mixtures thereof.

2. The process of claim 1 in which the catalyst is an oxide or carbonyl of tungsten, molybdenum or rhenium.

3. The process of claim 1 in which the catalyst is an oxide or carbonyl of rhodium, iridium, osmium, ruthenium, niobium, tantalum, tellurium, lanthanum, thorium, vanadium, or tin, either alone or in admixture with each other or with an oxide or carbonyl of tungsten, molybdenum or rhenium.

4. The process of claim 2 in which the catalyst is molybdenum or tungsten and is promoted with cobalt or chromium.

5. A process as claimed in claim 1 in which the catalyst is molybdenum hexacarbonyl or tungsten hexachloride or a mixture of the two.

6. A process as claimed in claim 1 carried out in the liquid phase.

7. A process as claimed in claim 1 carried out in the vapour phase.

8. The process of claim 5 in which the tungsten hexachloride is used in conjunction with a reducing agent.

* * * * *